(12) United States Patent
Ma

(10) Patent No.: US 8,374,690 B2
(45) Date of Patent: Feb. 12, 2013

(54) APPARATUS FOR DETERMINING HEALTH OF AN INDIVIDUAL

(75) Inventor: Z. Ming Ma, Shanghai (CN)

(73) Assignee: ARI Licensing, Warren, NJ (US)

( * ) Notice: Subject to any disclaimer, the term of this patent is extended or adjusted under 35 U.S.C. 154(b) by 743 days.

(21) Appl. No.: 12/381,293

(22) Filed: Mar. 10, 2009

(65) Prior Publication Data

US 2010/0234753 A1 Sep. 16, 2010

(51) Int. Cl.
*A61H 39/02* (2006.01)

(52) U.S. Cl. .................................................. 600/548

(58) Field of Classification Search ............... 600/547, 600/546, 595, 544, 493, 306
See application file for complete search history.

(56) References Cited

U.S. PATENT DOCUMENTS

| | | | |
|---|---|---|---|
| 5,058,583 A * | 10/1991 | Geddes et al. | 600/547 |
| 6,230,050 B1 * | 5/2001 | Pitts et al. | 600/547 |
| 6,336,045 B1 * | 1/2002 | Brooks | 600/547 |
| 6,415,176 B1 * | 7/2002 | Scheirer et al. | 600/547 |
| 6,546,270 B1 * | 4/2003 | Goldin et al. | 600/374 |
| 6,694,180 B1 * | 2/2004 | Boesen | 600/547 |
| 6,829,502 B2 * | 12/2004 | Hong et al. | 600/544 |
| 7,689,437 B1 * | 3/2010 | Teller et al. | 705/2 |
| 7,693,572 B2 * | 4/2010 | Kuramori et al. | 600/546 |
| 7,783,345 B2 * | 8/2010 | Skrabal et al. | 600/547 |
| 7,996,088 B2 * | 8/2011 | Marrosu et al. | 607/45 |
| 2003/0135097 A1 * | 7/2003 | Wiederhold et al. | 600/301 |
| 2004/0133081 A1 * | 7/2004 | Teller et al. | 600/300 |
| 2005/0240233 A1 * | 10/2005 | Lippert et al. | 607/6 |
| 2008/0319336 A1 * | 12/2008 | Ward et al. | 600/547 |

* cited by examiner

*Primary Examiner* — Brian Szmal
*Assistant Examiner* — Mehari Kidanemariam
(74) *Attorney, Agent, or Firm* — Henry T. Brendzel

(57) ABSTRACT

A method and apparatus for obtaining data relevant to the state of health of an individual by measuring the signal spectra at various points on the individual's body. Illustratively, the measurements are at points on the individual's hand, implemented with a glove that includes numerous electrical point contacts.

16 Claims, 2 Drawing Sheets

APPARATUS FOR DETERMINING HEALTH OF AN INDIVIDUAL

BACKGROUND

This relates to a method and apparatus for determining the health of an individual.

Chinese Medicine concepts and practices originated long before the onset of the modern fields of anatomy, physiology, surgery and other invasive diagnostic and healing techniques. Root-cause diagnosis of the illness is based on observations of the exogenous physical symptoms, such as the temperature, the facial appearance, perspiration, the heart-beat, breathing and the pulse rate patterns. Practitioners of Chinese Medicine combine these observations and knowledge accumulated through studies and practical experiences to locate the source and determine the causes of abnormality.

Definition and terminology for the anatomical organs according to Chinese Medicine differ from those in the modern physiology even though the domain of the overall coverage is the same. For example, the term heart is understood to include the heart, as is in the modem anatomy, and the auxiliary vascular and neuro-network systems. Since the heart cannot function without the support of its auxiliary systems Chinese Medicine implicitly recognizes the potential correlation of pathology of the anatomical heart and that of its auxiliary support systems.

It is also a Chinese Medicine concept that communications among the various organs are channeled through a complex network of Jing Lo. A person is expected to be in good physical health when communications flow unimpeded in Jing Lo, whereas a blocked or congested Jing Lo signifies ailment. Interconnectivity via the Jing Lo network implies that ailment in a given organ can and usually does involve multiple others.

According to the modem notions of anatomy, the human body can be said to comprise the skeletal frame with the attached muscle masses for movement and for mechanical support for other more localized organ systems, such as the digestive system, the respiratory system, the reproductive system and the urinary system. Interconnecting these localized systems are the cardiovascular system for the internal transport of blood, oxygen, and carbon dioxide, the endocrine system for integration and coordination of hormones, the lymphatic system for immunal regulation, and the nervous system for electrochemical signaling.

Although Jing Lo has not been identified with a definitive set of physical constituents in the human body, it is nonetheless reasonable to consider it as a virtual network of media capable of channeling signals between, and facilitating communications among organs.

The physics, particularly the electrical characteristics of several of the plausible constituents for this virtual network including the blood vassals, the nerves, the bones and the muscle masses have been extensively studied and modeled. For example, it is well known to nutritionists that the electrical equivalent for the muscle mass is a complex reactive network of resistance and capacitance, and that the electrical conductivity of blood is akin to a simple conductor with conductivity linear with the red cell counts. The fact that the muscle reactance can change with the ionic contents of its surrounding environment is also well known to physiologists that study narcosis. Animal studies have revealed that both for large and small animals the electrical impedance of the bone can be characterized by a simple network of resistors and capacitors.

Modeling of the electrical characteristics of the human cardiovascular system against known EKG data in the low frequency range of 120 Hz or below also exists in the literature. In the higher frequency domain up to 1 kHz, EKG (more commonly referred to as High Frequency Electrocardiography) studies seeking link it to better detection of Myocardial Ischemia and other coronary artery diseases is a hot research topic. However, we are not aware of any systematic electrical impedance information in the higher frequency ranges, regarding the cardiovascular network, nor the neural networks that interconnect multiple organs.

The physics of signal transmission in a single neuron takes on the characteristics of a complex electrical circuit with interesting features such as switching, tuning, and even resonances. Proper characterization of the neural network related to a given organ, and by inference, that portion of the Jing Lo system requires the analysis of its impedance spectra.

Chinese Medicine generally holds that Jing Lo evidences itself on the surface of the human body. These are referred to as the termination points. In fact, according to several schools of practitioners, a large collection of these termination points are present on the palm. For example, Jing Lo connected to the stomach terminates at the center of the palm whereas the heart evidences itself at the intersection of the backward extension of the thumb and the forefinger of the palm. The lungs are at the base of the fourth finger and the pinky. A correspondingly detailed map is believed to hold with foot hosting these Jing Lo termination points. The state of an individual's physical health can thus be gleaned via these termination points.

Since communications among all organs are channeled through the same Jing Lo network impedance spectra from a multitude of points on the human body will be needed in order to deduce information from any given organ. Put it another way. If one measures the impedance spectrum from a single termination point or a cluster of termination points in close proximity to a particular organ system, information one can glean from the data may be mostly from that particular organ system with minor interference or contamination from others. Such is the case with EKG or the EEG technologies. To eliminate superfluous or even misleading evidence due to mutual informational interference and distortion from other linked organ systems, a methodology and an apparatus is needed to collect data from a multitude of termination points for a multi-channel spectral analysis. Such is the intention and purpose of this patent disclosure.

SUMMARY OF THE INVENTION

Based on the Chinese Medicine concept of the Jing Lo network, we realized that the impedance spectral pattern on the hand, or foot, or any of the other areas of the body that contain numerous Jing Lo termination points can indicate whether the Jing Lo network is impeded in some way or not, and a person's health status can be assessed from the impedance spectral patterns. Accordingly, disclosed is a method and apparatus for obtaining data relevant to the state of health of an individual by measuring the signal spectra at various points on the individual's body. Illustratively, the measurements are at points on the individual's hand, implemented with a glove that includes numerous electrical point contacts, and the signals that are measured are reflective of impedances.

DETAILED DESCRIPTION

Figure 1:
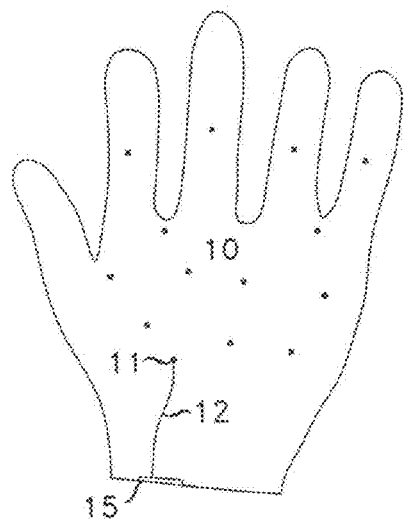
FIG. 1 illustrates a glove that may be used in connection with this invention.

As described above, it is known that Jing Lo reports on the status of all major human organs and other functional components of an individual, and that this status can be assessed through the Jing Lo network presence on surfaces of the skin that are rich with Jing Lo termination points (health-indicating surfaces, or HI surfaces) such as on the hands and/or the feet. It is also known that all systems of a body are characterized by electrical activity. We realized that the ancient art of Jing Lo can be combined with the more recent scientific findings about the systems of a body, and that the condition of the Jing Lo network can be quantitatively ascertained by measuring impedance at different points on HI surfaces, with the impedance at each point being measured for a preselected set of frequencies. This realization is supported by the fact that, as taught the generalized Thevenin's Theorem, any complex network of resistors, capacitors, inductors, gates and signal sources can be reduced to a simple network of complex impedance and gates plus a single signal source when viewed from two points of the circuit.

While concrete quantitative assessments are a hopeful goal, it is currently more realistic to set forth a comparative assessment. That is, in accord with one aspect of this disclosure, an individual's Jing Lo is measured, and a determination is made whether the individual is probably in good health or, to the contrary, that a part of the body (e.g., the liver) might be not in good health, based on a comparison to a selected norm. In one illustrative embodiment, the Jing Lo is reflected in impedances that exist at various points on an individual's HI surface(s) and, so, a set of impedance measurements is taken, the measurements are processed, and then compared to corresponding information from a statistically significant number of individuals of, for example, somewhat similar standing to that of the tested individual (e.g., ethnic background, sex, age), or to the data of past measurements of that same individual.

It should be perhaps emphasized that the method of this invention does not definitively state that an individual is well or is not; it is more an indication of probability. In that sense, this is not too unlike a conventional blood test that provides the physician with a plethora of indicators. As in a conventional blood test, where one indicator that is outside the accepted range does not mean that the individual is definitely sick, so an impeded Jing Lo does not indicate that the individual is definitely sick.

As indicated above, in one illustrative embodiment the Jing Lo is reflected in impedance that exists at various points on the HI surface. In order to determine the impedance of any particular point on the HI surface (relative to a selected common point), electric contact needs to be established with each of the particular points, much like the electric contacts in the case of EKG measurements. Since the Jing Lo extends beyond mere DC, measurement means may employ electrostatic and electromagnetic means.

FIG. 1 presents one illustrative embodiment in accord with the principles disclosed herein, where a glove 10 constitutes a Jing Lo Information Detector (JLID). Illustratively, the JLID glove is woven from non-conducting material, such as cotton, and it includes a number of electrical contact points (sensors) 11, such as copper rivets affixed to the inside of the glove. The glove is fashioned tight enough so that when wearing the glove, these sensors make good electrical contacts with the hand, e.g. the palm. A wire 12 is attached between each of the sensors and connector 15 so that the impedance measuring signals can flow to the measuring equipment. For a JLID that is used for a foot as a source of Jing Lo network presence, a sock of a similar design is used.

Figure 2:
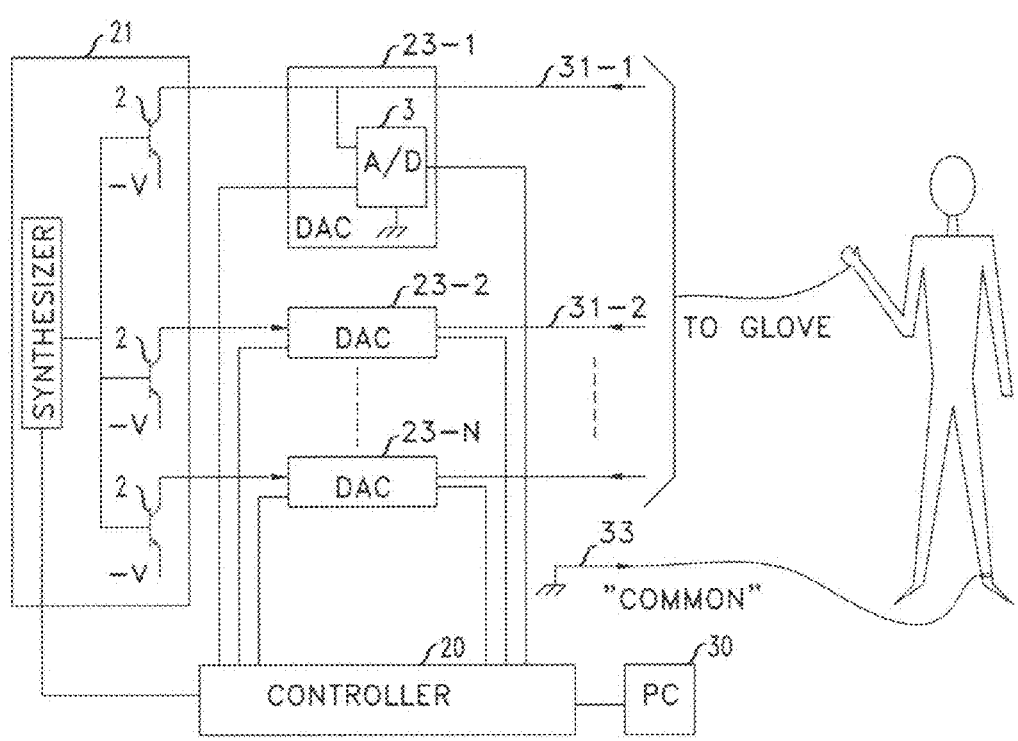
FIG. 2 is a block diagram of one apparatus embodiment in accord with the principles of this invention.

FIG. 2 presents an illustrative block diagram of the measuring equipment, which is driven by controller 20. Specifically controller 20 directs a synthesizer within distributor 21 to generate a voltage of a particular frequency. That voltage, generated in a conventional manner, is converted to a plurality of current sources by means of transistors 2 and are each applied to one of identical data acquisition circuits (DAC) 23-$i$. DAC circuit 23-1, illustrated in FIG. 2, simply applies the current injected by distributor 21 to line 31-1. Line 31-1 is connected to one of the sensors in glove 10 and when a patient puts the glove on and a ground line 33 is attached to a preselected point on the body (for example, to the ankle opposite the hand that wears the glove) the current that is caused to flow through line 31-1 creates a voltage relative to ground that is directly proportional to the current I(f) sent through line 31-1 and the impedance Z(f) between the sensor and ground. DAC 23-1 includes a conventional A/D converter 3 that senses the voltage under direction of controller 20, converts it to digital format, and offers it to controller 20. Of course, in applications where it is believed that the signal to be A/D converted contains significant energy at frequencies above half the sampling rate of the A/D converter, an appropriate filter may be included to precede the A/D converter to prevent contamination. Lastly, the measurements obtained by controller 20 are provided to processor 30 (illustratively, a personal computer) for analysis.

It is noted that when using a current of one given magnitude it is possible to speak in terms of voltage, rather than impedance, and decisions about the Jing-Lo can be made strictly on the basis of voltages, recognizing that the voltages are surrogates for impedances.

In applications where it is considered advantageous to detect all signals at the same instances, the A/D converters are controlled to capture their respective signals concurrently, and to then compute the digital representations of the captured signals and apply those digital representations to the controller. It is also possible to employ sample-and-hold circuit instead of individual A/D converter 3 in DACs 23-$i$, to sample and hold the voltages simultaneously, or otherwise (as desired) and to apply the analog signals to a single A/D converter that is situated within controller 20 in a seriatim fashion.

Obviously, when using a single A/D converter, it needs to be fast enough to accommodate a sampling rate that is appropriate for the highest frequency of interest; that is, for a maximum frequency $f_{max}$, each point needs to be sampled at the rate of at least $2f_{max}$, and if the voltages of N points are converted by a single A/D converter, it needs to perform a conversion in not more than $\frac{1}{2}Nf_{max}$ seconds.

Synthesizer 21 is configured to generate a sequence of signals each at a different frequency. In an alternative embodiment synthesizer 21 may be configured to generate a signal that contains all of the frequencies of interest. The A/D in such an embodiment develops measures of the created voltages periodically, at a rate that is at least twice the highest frequency of interest, and controller 20 effectively computes the response at the different frequencies, as is well known in the art (e.g., employing the FFT algorithm).

A test session consists of the patient wearing the JLID device and controller 20 directing synthesizer 21 to apply a sequence of signals at different frequencies, and each such signal is, in turn, converted to a current and sent over a different one of the lines 31-*i* to the JLID. The controller collects the voltage readings of the A/D converters and applies them to PC 30.

In accord with the principles of this disclosure the information thus obtained by PC 30 is processed to identify statistically significant deviations from at least a primary data set that indicates whether the tested individual is probably in good health, or perhaps not. One such data set that is contemplated herein is the data set of past measurements of the individual when that individual was considered healthy. Alternatively, the data set may the set of measurements of a large group of individuals that are considered healthy. This large group may be undifferentiated, or perhaps chosen to be most like the individual; for example, in terms of ethnic background, sex, age, etc. Additional data sets may be constituted of individuals with specific known maladies; for example, people suffering from Crohn's disease.

Illustratively, newly acquired data at PC 30 can be assessed by initially evaluating whether the measurement at each of the sensor points, $Z_{input}(f, m)$, where f is the frequency and m identifies the sensor, differs to a statistically significant extent from a set corresponding measurements $\{Z_{primary}(f, m)\}$ of the primary database. This is a very basic statistical determination that is well known in the art. Such an initial assessment simply determines whether there is any need for further processing.

Figure 3:
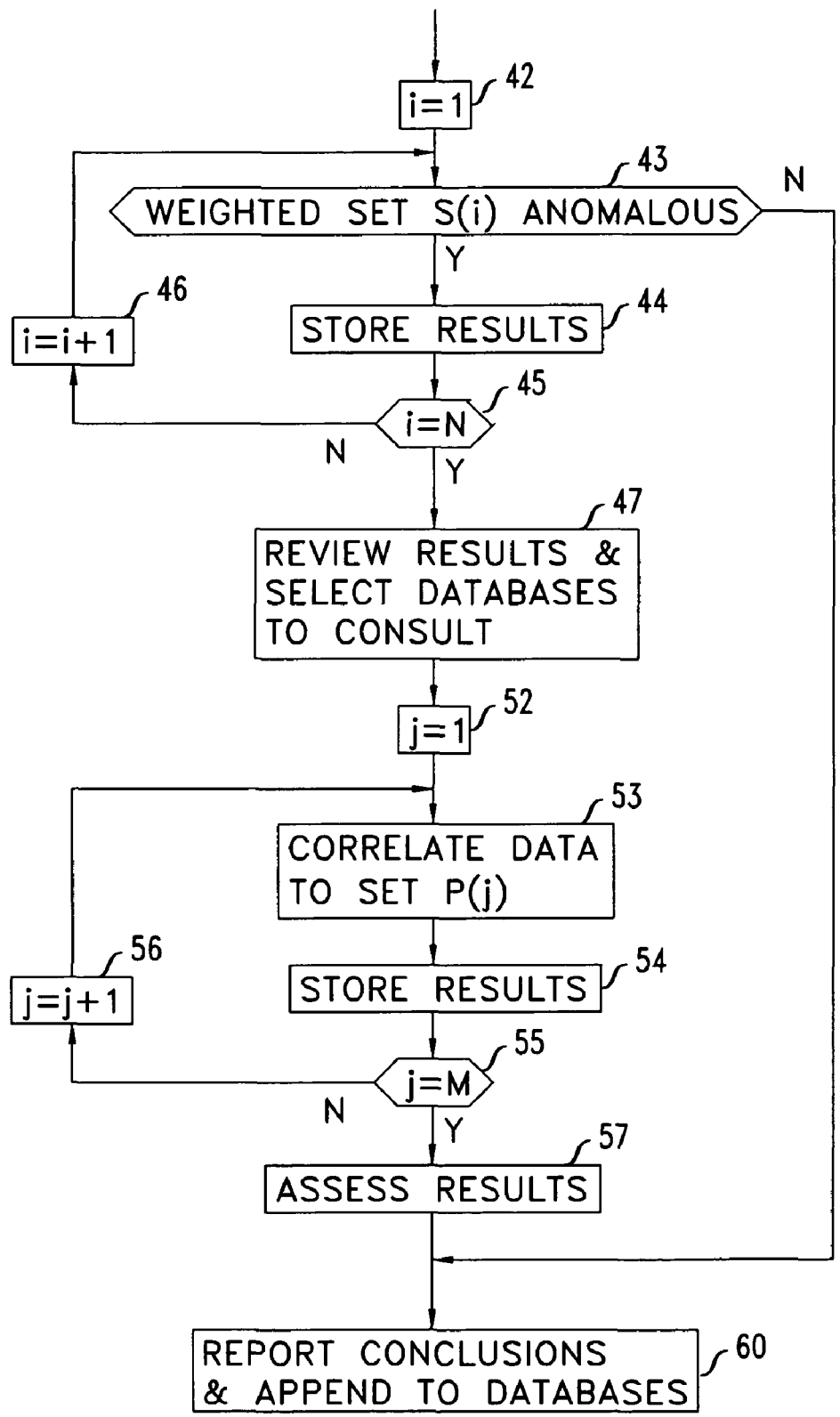
FIG. 3 is a block diagram of a method in accord with the principles of this invention.

Since according to Jing Lo principles each of the body systems has numerous appearances in an HI surface (e.g., a person's skin), it is advantageous to assess a particular body system on the basis of a set of measurements, rather than measurements of individual points. FIG. 3 presents a flowchart of one method in accord with the principles disclosed herein where weighted sets of the voltage measurements are assessed. If different body systems that might be assessed are identified by index i, when a given body system is to be assessed an appropriate set s(i) of measuring points m is selected from among the entire collection of measuring points, a measurement $Z_{input}(f, m_k)$ is obtained at each of those measurement points, $m_k$, (index k identifies the particular point), and a signal that is a function of all of the measuring points, $Z_{s(i)}(f)=H(Z_{input}(f, m_k))$ is developed and assessed. Illustratively, the function can be the weighted sum $$Z_{s(i)}(f) = \sum_k a(i, m_k) Z_{input}(f, m_k)$$

over the measurement points of set s(i), where $a(i, m_k)$ is the multiplicative weight that reflects how strong is the association known to be between the body system i and measurement point $m_k$.

The FIG. 3 method measures all body systems and, accordingly, at step 42 a set i is chosen and control passes to step 43 where $Z_{s(i)}(f)$ is evaluated to determine whether it differs—to a statistically significant extent—from $$Z_{primary}(f) = \sum_k a(i, m_k) Z_{primary}(f, m_k).$$

The results are stored in step 44 and control passes to step 45 which determines whether all sets have been considered (i=N). If not the index i is incremented in step 46 and control returns to step 43. When all sets have been considered, control passes to step 47.

It should be noted that the measurement assessments mentioned above may be performed at one particular frequency, at a set of frequencies, or at an entire range of frequencies, either seriatim or concurrently as disclosed above.

Step 47 reviews the results and determines whether, on balance, the state of the different body systems as represented by the input data represents a state of good health or not. The results of step 47 actually points to a particular body system that may have a problem, but generally it does not provide a good indication of the specific malady that may exist.

Knowing that something is not quite right with a particular body system is of tremendous benefit, but obtaining a specific diagnosis of a malady is much better. To that end, the flowchart of FIG. 3 continues to the segment that includes steps 52-57 where a better analysis is obtained by correlating the available data with corresponding data of people who have had specific problems with a similar presentation of the Jing Lo network. Accordingly, in step 52 one of a set of specific of measuring points is chosen and control passes to step 53. At step 53 a database of measurements information is retrieved by PC 30 (either from its own storage or, more likely, from a national database) and the measurements obtained from the tested individual are correlated to that data in the retrieved database information. Control then passes to step 54 which stores the correlation results and, thence, to step 55, which determines whether all of the specific problems in the selected set have been considered. If not, control passes to step 56 where the index j is incremented and then returned to step 53 to repeat the correlation relative to the information in a database associated with a different specific malady.

When all of the specific maladies in the set have been considered, control passes from step 55 to step 57, where the results of the correlations are assessed. Lastly, control passes to step 60 where the results are reported to the individual, and the data set of measurements is appended at least to the primary database.

It may be noted that patient privacy laws may dictate that the newly acquired patient information, and certainly the collection of previously acquired patient information, may not be permanently stored in PC 30. This is not a significant issue, however, because the patient information can be stored in a simple USB drive or a smart card that the patient maintains and provides to the tester as necessary.

It is noted that the measurements spectra as they appear at different termination point pairs (i.e., where the measurement points are and where the "common" point is) represent different views of the same Jing Lo network. Some such spectrum is expected to be more sensitive to certain organs than others. For example, the spectrum taken on the chest is likely to be richer in heart information contents. A significant correlation of these spectra between that of an individual and a clinical sample of patients with particular disease state are powerful means of ascertaining the state of health of that individual. Therefore, in accord with an additional aspect of this disclosure, a first set of measurements and assessments are made with a particular Jing Lo Information Detector, and when a more fine-tuned assessment of a particular body system is desired, another set of measurements is taken using a different Jing Lo Information Detector, a different "common" point, or both.

It should be kept in mind that the Jing Lo information Detector of FIG. 1 is merely illustrative; not only in the sense that it is a glove rather than a sock or some other device that can attach to a body part (e.g., chest), but also in that the measuring points can be accessed capacitively, or electromagnetically rather than through an intimate physical and electrical (DC) contact. A form that was implemented, for developing this invention uses an off-axis parabolic reflector for detecting electromagnetic radiation from the body, similar that of a parabolic dish antenna receiving electromagnetic signal from a remote satellite. An advantage of electromagnetic coupling to measuring points is that the measuring points may be other than termination points on a person's skin; for example the pupil of an eye.

In the context of this disclosure, connectivity that encompasses DC, capacitive coupling, inductive coupling and electromagnetic coupling is terms "electronic coupling."

Likewise, it should be kept in mind that FIG. 2 is illustrative for embodiments that comprise an explicit set of current sources that create voltages at the measuring points (relative to the "common" point). Another embodiment that is different in kind (rather than just in detail) is an embodiment where advantage is taken of voltages that already exist in a body. Two illustrations of such voltages are the voltages induced by the household power grid (60 Hz in the US) and voltages created by the heart system. In embodiments that use the voltages created by the heart system, for example, the FIG. 2 apparatus degenerates to just the DAC, controller 20, and PC 30.

The $Z_{input}(f, m_k)$ information that is developed above is the combined spectrum information spanning the entire frequency band. However, just as in the of field of genetics where it is possible to focus attention only on specific chromosome sequences rather than looking at the entire genome, it is possible in the Join Lo network to focus on a certain group of frequencies. It ought to be noted, also, that while the measurements discussed above are frequency domain measurements, but it is possible to employ other domains, such as time.

The invention claimed is:

1. Apparatus comprising:
   a device that includes an N plurality of disjoint sensors, which device is adapted to electronically couple each of said sensors to specific locations on an exterior surface of an individual that is to interface with said apparatus;
   a module that is configured to apply energy to said sensors, where the energy at each sensor is characterized by a spectrum that contains a preselected set of frequencies of interest, and
   a processing device that is configured to take action pertaining to well-being of said individual when values of elements of frequency spectra associated with a subset of said sensors differ to a statistically significant extent from a set of frequency spectrum element values obtained from a database of health-related information, where said subset includes at least one and at most N of said sensors.

2. The apparatus of claim 1 where the action taken by said processing device is configured to reach a conclusion regarding state of said individual's health.

3. The apparatus of claim 1 further comprising an electrical contact element constructed to couple to a location on said individual's skin; said module that configure to apply energy between each of the sensors and said electrical contact element.

4. The apparatus of claim 3 where said device is configured to be held in close proximity with a surface of one or more of an individual's body parts taken from a set that includes a palm, a leg, a chest, a head, and a back.

5. The apparatus of claim 4 where said energies are currents that said module causes to flow between said sensors and a common point, and said determined spectra of said concurrent responses are relative to said common point.

6. The apparatus of claim 1 where said values of elements of frequency spectra associated with said subset of sensors are frequency spectra of impedances of said sensors said processing device is configured to compute, and said a set of frequency spectrum element values obtained from said database information comprise frequency elements.

7. The apparatus of claim 1 where the values obtained from said database are related to nature of health test to which said individual is chosen to be subjected.

8. The apparatus of claim 7 where the energy that is applied by said module to said sensors is related to said nature of said health test.

9. The apparatus of claim 7 where said nature of said health test pertains to a specific health condition.

10. The apparatus of claim 7 where said nature of said health test pertains to one or more attributes of said individual.

11. The apparatus of claim 7 where said database is searchable based on attributes, including age, sex, ethnic identity, or nature of sickness.

12. The apparatus of claim 7 where said database, containing spectra information, is searchable based on attributes taken from a set that comprises age, sex, ethnic identity, and nature of sickness.

13. The apparatus of claim 1 where said values of elements of frequency spectra associated with the subset of said sensors are frequency spectrum components in a weighted sum of spectra of said subset of sensors.

14. The apparatus of claim 1 where said module comprises N>1 controllable current sources that are respectively connected to said N sensors to cause a current to flow between said N sensors and one common point in accord with a control signal that is applied to each of said N controllable current sources.

15. The apparatus of claim 1 where said module is configured to apply a group of frequencies one frequency at a time.

16. The apparatus of claim 1 where
   said subset of said sensors is chosen according a particular health-related test that is desired to be applied to said individual to assess said individual's well-being; and
   said health-related information chosen from said database is chosen according to said particular health-related test and attributes that pertain to said individual.

* * * * *